(12) United States Patent
Urihara et al.

(10) Patent No.: US 8,592,461 B2
(45) Date of Patent: Nov. 26, 2013

(54) PLANT DISEASE CONTROL AGENT

(75) Inventors: Ichirou Urihara, Tokyo (JP); Atsunori Isshiki, Yokohama (JP); Hiroyasu Hosokawa, Fujieda (JP); Tomoyuki Saiga, Makinohara (JP)

(73) Assignee: Nippon Soda Co., Ltd., Tokyo (JP)

( * ) Notice: Subject to any disclaimer, the term of this patent is extended or adjusted under 35 U.S.C. 154(b) by 273 days.

(21) Appl. No.: 12/934,004

(22) PCT Filed: Mar. 24, 2009

(86) PCT No.: PCT/JP2009/001302
§ 371 (c)(1),
(2), (4) Date: Sep. 22, 2010

(87) PCT Pub. No.: WO2009/119072
PCT Pub. Date: Oct. 1, 2009

(65) Prior Publication Data
US 2011/0159110 A1   Jun. 30, 2011

(30) Foreign Application Priority Data
Mar. 24, 2008   (JP) ................................. 2008-075748

(51) Int. Cl.
| | |
|---|---|
| *A01N 37/34* | (2006.01) |
| *A01N 37/46* | (2006.01) |
| *A01N 43/36* | (2006.01) |
| *A01N 43/38* | (2006.01) |
| *A01N 43/40* | (2006.01) |
| *A01N 43/54* | (2006.01) |
| *A01N 43/50* | (2006.01) |
| *A01N 43/653* | (2006.01) |
| *A01N 43/713* | (2006.01) |
| *A01N 43/78* | (2006.01) |
| *A01N 47/10* | (2006.01) |
| *A01N 47/44* | (2006.01) |

(52) U.S. Cl.
USPC ........... 514/340; 514/141; 514/269; 514/336; 514/342; 514/365; 514/370; 514/381; 514/382; 514/383; 514/397; 514/417; 514/422; 514/479; 514/494; 514/525; 424/632

(58) Field of Classification Search
USPC .............. 514/340, 229.2, 141, 269, 336, 342, 514/365, 370, 381, 383, 397, 417, 422, 479, 514/492, 494, 525, 528, 538, 594, 635; 424/632
See application file for complete search history.

(56) References Cited

U.S. PATENT DOCUMENTS

| | | |
|---|---|---|
| 2005/0070439 A1 | 3/2005 | Kobori et al. |
| 2008/0153702 A1* | 6/2008 | Voeste et al. ............ 504/100 |
| 2012/0027741 A1 | 2/2012 | Coqueron et al. |

FOREIGN PATENT DOCUMENTS

| | | |
|---|---|---|
| JP | 02-049708 | 2/1990 |
| JP | 02-196701 | 8/1990 |
| JP | 2000-509062 | 7/2000 |
| JP | 2001-505886 | 5/2001 |
| JP | 2002-193713 | 7/2002 |
| JP | 2002-193714 | 7/2002 |
| JP | 2002-193715 | 7/2002 |
| JP | 2002-193716 | 7/2002 |
| KR | 2000-0065014 | 11/2000 |
| WO | 97/40678 | 11/1997 |
| WO | 98/25465 | 6/1998 |
| WO | WO 03/016303 | 2/2003 |
| WO | 2006/069716 | 7/2006 |
| WO | 2009/090181 A2 | 7/2009 |
| WO | WO 2009/090181 * | 7/2009 |

OTHER PUBLICATIONS

HCAPLUS abstract 2006:815962 (2006).*
International Search Report and Written Opinion, International PCT Application No. PCT/JP2009/001302, mailed Jun. 16, 2009 (English-language translation provided).
Preliminary Report on Patentability, International PCT Application No. PCT/JP2009/001302, mailed Nov. 9, 2010 (English-language translation provided).
Japanese Office Action issued for JP 2010-505338, dated Oct. 16, 2012, 8 pages (with English translation).
EP Communication including Supplementary European Search Report from EP Appln. No. 09726026, Nov. 16, 2012, 6 pages.
Japanese Office Action issued for JP 2010-505338, dated Jul. 17, 2012, 10 pages (with English translation).
Korean Office Action issued for KR 2010-7020856, dated Aug. 14, 2012, 8 pages (with English translation).
Notice of Allowance issued on Oct. 3, 2013 in U.S. Appl. No. 13/938,896.

* cited by examiner

*Primary Examiner* — John Pak
(74) *Attorney, Agent, or Firm* — Kenyon & Kenyon LLP

(57) ABSTRACT

The present invention provides a plant disease control agent containing at least one of tetrazoyloxime dirivatives and salts thereof, and at least one selected from the group consisting of fosetyl, propamocarb, basic copper chloride, chlorothalonil, manzeb, cymoxanil, folpet, iminoctadine, cyazofamid, metalaxyl, fludioxonil, tebuconazole, prothioconazole, thiamethoxam, azoxystrobin and salts thereof.

1 Claim, No Drawings

PLANT DISEASE CONTROL AGENT

TECHNICAL FIELD

The present invention relates to a plant disease control agent containing tetrazoyloxime derivative or the like and an active ingredient for agricultural and horticultural use.

Priority is claimed on Japanese Patent Application No. 2008-075748, filed Mar. 24, 2008, the content of which is incorporated herein by reference.

BACKGROUND ART

Until now, in the cultivation of agricultural and horticultural crops, although a large number of disease control agents are used against crop disease, since the control effects thereof may be inadequate, the use thereof may be restricted due to the appearance of agrichemical-resistance pathogenic organisms, the plants may be damaged or contaminated by the agrichemical or the agrichemical may demonstrate toxicity to humans, livestock or marine life, a considerable number of these disease control agents are not necessarily considered to be satisfactory. Thus, there is a need to develop a plant disease control agent that can be used safely and has few of these shortcomings.

The present inventors carried out exhaustive research in view of the above-described circumstances, and discovered that tetrazoyloxime derivative and/or the salt thereof are useful as an active ingredient of plant disease control agent, and previously filed a patent application (Patent Document 1).

[Patent Document 1] International Publication No. WO03/016303

DISCLOSURE OF INVENTION

Problems to be Solved by the Invention

The present invention was carried out as a part of research on a plant disease control agent containing tetrazoyloxime derivative and/or the salt thereof described in Patent Document 1 as an active ingredient and an objective of present invention is to provide a plant disease control agent that demonstrates excellent control effects against plant disease at low doses.

BEST MODE FOR CARRYING OUT THE INVENTION

In order to solve the aforementioned objective, the present inventors further carried out extensive research on a plant disease control agent containing tetrazoyloxime derivative and/or salt thereof described in Patent Document 1 as an active ingredient. As a result, the inventors of the present invention found that superior control effects against plant disease at low doses can be obtained by using the said tetrazoyloxime derivative and/or salt thereof together with an other fungicidal active ingredients for agricultural and horticultural use, thereby leading to completion of the present invention.

Thus, the present invention provides a plant disease control agent containing at least one of tetrazoyloxime derivative represented by a formula (1)

[Chemical formula 1]

{In the formula, X represents hydrogen atom, an unsubstituted or substituted C1 to C6 alkyl group, an unsubstituted or substituted C1 to C6 alkoxy group, halogen atom, nitro group, cyano group, an unsubstituted or substituted aryl group, or an unsubstituted or substituted C1 to C6 alkyl sulfonyl group. q represents an integer of 0 to 5. A represents a tetrazoyl group represented by a formula (2) or (3)

[Chemical formula 2]

(In the formula, Y represents a C1 to C6 alkyl group), D represents a group represented by a formula (4) or (5)

[Chemical formula 3]

[In the formula, Z represents hydrogen atom, an amino group or a group represented by a formula —NHC(=O)-Q (In the formula, Q represents hydrogen atom, a C1 to C8 alkyl group, a C1 to C6 haloalkyl group, a C3 to C6 cycloalkyl group, a C1 to C8 alkoxy group, a C3 to C6 cycloalkyloxy group, a C7 to C20 aralkyloxy group, a C1 to C4 alkyl thio C1 to C8 alkyl group, a C1 to C4 alkoxy C1 to C2 alkyl group, a C1 to C4 acyl amino C1 to C6 alkyl group, a C1 to C4 acyl amino C1 to C6 alkoxy group, a C1 to C8 alkyl amino group, a C2 to C6 alkenyl group, a C7 to C20 aralkyl group or a C6 to C10 aryl group). R represents hydrogen atom or a halogen atom.]} and salts thereof, and at least one selected from the group consisting of fosetyl, propamocarb, basic copper chloride, chlorothalonil, manzeb, cymoxanil, folpet, iminoctadine, cyazofamid, metalaxyl, fludioxonil, tebuconazole, prothioconazole, thiamethoxam, azoxystrobin and salts thereof.

Effects of the Invention

The plant disease control agent of the present invention demonstrates excellent control effects against plant disease at low doses, and eliminates concern over chemical damage to useful plants.

BEST MODE FOR CARRYING OUT THE INVENTION

The following provides a detailed explanation of the present invention.

The plant disease control agent of the present invention contains at least one of tetrazoyloxime derivatives represented by the formula (1) and salts thereof, and at least one of other fungicidal active ingredients for agricultural and horticultural use.

(1) Tetrazoyloxime Derivative and Salt Thereof

In the formula (1), X represents hydrogen atom, an unsubstituted or substituted C1 to C6 alkyl group, an unsubstituted or substituted C1 to C6 alkoxy group, a halogen atom, nitro group, cyano group, an unsubstituted or substituted aryl group or an unsubstituted or substituted C1 to C6 alkyl sulfonyl group.

Examples of C1 to C6 alkyl group of unsubstituted or substituted C1 to C6 alkyl group of X include methyl group, ethyl group, n-propyl group, i-propyl group, n-butyl group, s-butyl group, i-butyl group, t-butyl group, n-pentyl group, n-hexyl group and the like.

Examples of C1 to C6 alkoxy group of unsubstituted or substituted C1 to C6 alkoxy group of X include methoxy group, ethoxy group, n-propoxy group, i-propoxy group, n-butoxy group, s-butoxy group, i-butoxy group, t-butoxy group and the like.

Examples of substituents of C1 to C6 alkyl group and C1 to C6 alkoxy group are not limited as long as the substituents are chemically acceptable, although they include a halogen atom such as fluorine atom, chlorine atom, bromine atom or iodine atom; a C1 to C6 alkoxy group such as methoxy group, ethoxy group, n-propoxy group, i-propoxy group, n-butoxy group, s-butoxy group, i-butoxy group or t-butoxy group; an unsubstituted or substituted phenyl group such as phenyl group, 4-methyl phenyl group, 2-chlorophenyl group; nitro group; cyano group; an unsubstituted or substituted amino group such as amino group, methyl amino group, dimethyl amino group, acetyl amino group or benzoyl amino group.

Examples of halogen group of X include fluorine atom, chlorine atom, bromine atom, iodine atom and the like.

Examples of aryl group of unsubstituted or substituted aryl group are not particularly limited, although a C6 to C10 aryl group is preferable. More specifically, phenyl group, 1-naphthyl group, 2-naphthyl group and the like may be cited.

The substituents of aryl group are not limited as long as the substituents are chemically acceptable. Examples of the substituents include a halogen atom such as fluorine atom, chlorine atom, bromine atom or iodine atom; a C1 to 6 alkyl group such as methyl group, ethyl group, n-propyl group, i-propyl group, n-butyl group, s-butyl group, i-butyl group, t-butyl group, n-pentyl group or n-hexyl group;

a C2 to 6 alkenyl group such as vinyl group, 1-propenyl group, 2-propenyl group, 1-butenyl group, 2-butenyl group, 3-butenyl group, 1-pentenyl group, 2-pentenyl group, 3-pentenyl group, 4-pentenyl group, 1-hexenyl group, 2-hexenyl group, 3-hexenyl group, 4-hexenyl group or 5-hexenyl group;

a C2 to 0.6 alkynyl group such as ethynyl group, 1-propynyl group, 2-propynyl group, 1-butynyl group, 2-butynyl group, 3-butynyl group, 1-pentynyl group, 2-pentynyl group, 3-pentynyl group or 4-pentynyl group;

a C1 to 6 alkoxy group such as methoxy group, ethoxy group, n-propoxy group, i-propoxy group, n-butoxy group, s-butoxy group, i-butoxy group or t-butoxy group;

nitro group; cyano group; and the like.

Examples of C1 to c6 alkyl sulfonyl group of unsubstituted or substituted C1 to C6 alkyl sulfonyl group of X include methyl sulfonyl group, ethyl sulfonyl group, n-propyl sulfonyl group, i-propyl sulfonyl group and the like.

The substituents of the C1 to C6 alkyl sulfonyl group are not particularly limited as long as they are chemically acceptable and examples of the substituents are the same as the examples of the substituents of C1 to C6 alkyl group of X.

q represents an integer of 0 to 5, preferably represents 0 or 1, and more preferably represents 0.

When q is 2 or more, plural Xs may be the same or different.

A represents a tetrazoyl group represented by the formula (2) or (3).

In the formula (2) or (3), Y represents an alkyl group such as methyl group, ethyl group, n-propyl group, i-propyl group, n-butyl group, s-butyl group, i-butyl group, t-butyl group, n-pentyl group or n-hexyl group.

D represents a group represented by the formula (4) or (5).

Z represents hydrogen atom, an amino group or a group represented by the formula: —NHC(=O)-Q.

Q represents hydrogen atom, a C1 to C8 alkyl group, a C1 to C6 haloalkyl group, a C3 to C6 cycloalkyl group, a C1 to C8 alkoxy group, a C3 to C6 cycloalkyloxy group, a C7 to C20 aralkyloxy group, a C1 to C4 alkyl thio C1 to C8 alkyl group, a C1 to C4 alkoxy C1 to C2 alkyl group, a C1 to C4 acyl amino C1 to C6 alkyl group, a C1 to C4 acyl amino C1 to C6 alkoxy group, a C1 to C8 alkyl amino group, a C2 to C6 alkenyl group, an aralkyl group or an aryl group.

Examples of C1 to C8 alkyl group of Q include methyl group, ethyl group, n-propyl group, isopropyl group, 1,1-dimethyl propyl group, n-butyl group, isobutyl group, sec-butyl group, t-butyl group, isoamyl group, 1-methyl butyl group, 2-methyl butyl group, neopentyl group, 1-ethyl propyl group, n-pentyl group, n-hexyl group, n-heptyl group, n-octyl group and the like.

Examples of C1 to C6 haloalkyl group of Q include chloromethyl group, difluoromethyl group, trifluoromethyl group, difluorochloromethyl group, pentafluoroethyl group, 3,3,3-trifluoro-n-propyl group, 1-chlorohexyl group and the like.

Examples of C3 to C6 cycloalkyl group of Q include cyclopropyl group, cyclobutyl group, cyclopentyl group, cyclohexyl group and the like.

Examples of C1 to C8 alkoxy group of Q include methoxy group, ethoxy group, propoxy group, isopropoxy group, 1,1-dimethyl propoxy group, butoxy group, isobutoxy group, s-butoxy group, t-butoxy group, i-pentyloxy group, 1-methyl butoxy group, 2-methyl butoxy group, neopentyloxy group, 1-ethyl propoxy group, n-pentyloxy group, n-hexyloxy group, n-heptyloxy group, n-octyloxy group and the like.

Examples of C3 to C6 cycloalkyloxy group of Q include cyclopropyloxy group, cyclobutyloxy group, cyclopentyloxy group, cyclohexyloxy group and the like.

Examples of C7 to C20 of aralkyloxy group of Q include benzyloxy group, phenethyloxy group and the like.

Examples of C1 to C4 alkylthio C1 to C8 alkyl group of Q include methyl thiomethyl group, 2-methyl thio ethyl group, ethyl thiomethyl group, butyl thiomethyl group and the like.

Examples of C1 to C4 alkoxy C1 to C2 alkyl group of Q include methoxymethyl group, ethoxymethyl group, 2-methoxyethyl group, 2-ethoxyethyl group, n-butoxymethyl group and the like.

Examples of C1 to C4 acyl amino C1 to C6 alkyl group of Q include acetyl aminomethyl group, 2-(propionyl amino) ethyl group, 3-(acetyl amino)propyl group, 3-(propionyl amino)propyl group, 3-(pivaloyl amino)propyl group, 4-(acetyl amino)butyl group, 5-(acetyl amino)pentyl group, 6-(acetyl amino)hexyl group and the like.

Examples of C1 to C4 acyl amino C1 to C6 alkoxy group of Q include acetyl aminomethoxy group, 2-(propionyl amino) ethoxy group, 3-(acetyl amino)propoxy group, 3-(propionyl amino)propoxy group, 3-(pivaloyl amino)propoxy group and the like.

Examples of C1 to C8 alkyl amino group of Q include methyl amino group, ethyl amino group, n-propyl amino group, i-propyl amino group, n-butyl amino group, i-butyl amino group, s-butyl amino group, t-butyl amino group, neopentyl amino group, 1-ethyl propyl amino group, n-pentyl amino group, n-hexyl amino group, n-heptyl amino group, n-octyl amino group and the like.

Examples of C2 to C6 alkenyl group of Q include allyl group, i-propenyl group, 1-butenyl group, 2-butenyl group, 2-pentenyl group, 5-hexenyl group and the like.

Examples of C7 to C20 aralkyl group of Q include benzyl group, phenethyl group, 3-phenyl propyl group, 1-naphthyl methyl group, 2-naphthyl methyl group and the like.

Examples of C6 to C10 aryl group of Q include phenyl group, 1-naphthyl group, 2-naphthyl group and the like.

R represents hydrogen atom; or a halogen atom such as fluorine atom, chlorine atom or bromine atom.

The salts of tetrazoyloxime derivative represented by the formula (1) are not particularly limited as long as they are agriculturally and horticulturally acceptable. Examples of the salts include a salt of inorganic acids such as hydrochlorides, nitrates, sulfates or phosphates; and a salt of organic acids such as acetates, lactates, propionates or benzoates.

(E)-form and (Z)-form stereoisomers exist in the tetrazoyloxime derivative represented by the aforementioned formula (1) based on carbon-nitrogen double bonds. These two stereoisomers along with mixtures thereof are also included in the present invention. Synthetic products are normally obtained in the form of the (Z)-form only or as a mixture of the (E)-form and (Z)-form. The two isomers can be respectively isolated from a mixture of the (E)-form and (Z)-form by separating in accordance with known techniques such as silica gel column chromatography.

The (Z)-form of the tetrazoyloxime derivative represented by the formula (1) used in the present invention, and salts thereof, has superior plant disease control effects as compared with the (E)-form. However, since the (Z)-form is partially converted to the (E)-form due to the action of light and the like in the natural environment, and tends to stabilize at a constant ratio in the form of a mixture of the (E)-form and the (Z)-form, both of these compounds as well as mixtures thereof are useful. Furthermore, since the stable ratio of the (E)-form to the (Z)-form varies according to individual compounds, it cannot be universally specified.

The tetrazoyloxime derivative represented by the formula (1) and salt thereof may be produced, for example, by a method described in WO03/016303.

Examples of the tetrazoyloxime derivative represented by the formula (1) include compounds described in WO03/016303.

(2) Other Fungicidal Active Ingredient for Agricultural and Horticultural Use

The plant disease control agent of the present invention includes the above-described tetrazoyloxime derivative and salt thereof (hereinafter, referred to as "tetrazoyloxime derivatives"), as well as at least one selected from the group consisting of fosetyl, propamcarb, basic copper chloride, chlorothalonil, manzeb, cymoxanil, folpet, iminoctadine, cyazofamid, metalaxyl, fludioxonil, tebuconazole, prothioconazole, thiamethoxam, azoxystrobin, and salts thereof.

In addition, the above-described active ingredient compound may also include optically-active compounds thereof. For example, the active ingredient compound may include metalaxyl M which corresponds to metalaxyl.

The plant disease control agent of the present invention may properly be used together with other agrichemical active ingredients other than those agrichemical active ingredients listed above, and specifically, the examples thereof include the active ingredients described below.

In addition, the active ingredients are described by their generic name

Examples of active ingredient compounds of antimicrobial agents (generic name, including those for which application is currently pending) include:

anilinopyrimidine-based compounds such as mepanipyrim, pyrimethanil or cyprodinil;

pyridinamine-based compounds such as fluazinam;

azole-based compounds such as triadimefon, bitertanol, triflumizole, etaconazole, propiconazole, penconazole, flusilazole, myclobutanil, cyproconazole, hexaconazole, furconazole-cis, prochloraz, metconazole, epoxiconazole, tetraconazole, oxpoconazole fumarate, sipconazole, triadimenol, flutriafol, difenoconazole, fluquinconazole, fenbuconazole, bromuconazole, diniconazole, tricyclazole, probenazole, simeconazole, pefurazoate, ipconazole, imibenconazole or imazalil;

quinoxaline-based compounds such as quinomethionate;

dithiocarbamate-based compounds such as maneb, zineb, polycarbamate, metiram, propineb, ferbam, nabam, metam, thiram or ziram;

organic chlorine-based compounds such as fthalide or quintozene;

imidazole-based compounds such as benomyl, thiophanate-methyl, carbendazim, thiabendazole or fuberiazole;

phenylamide-based compounds such as mefenoxam, oxadixyl, ofurace, benalaxyl, benalaxyl-M, furalaxyl or cyprofuram;

sulfenic acid-based compounds such as dichlofluanid;

nitrophenyl-based compounds such as dinocap;

copper-based compounds such as cupric hydroxide or oxine copper;

isoxazole-based compounds such as hymexazol;

organic phosphorous-based compounds such as tolcofos-methyl, S-benzyl-O,O-diisopropyl phosphorothioate, O-ethyl-S,S-diphenyl phosphorodithioate or aluminum ethyl hydrogen phosphonate;

N-halogenothioalkyl-based compounds such as captan or captafolt;

dicarboxylmide-based compounds such as procymidone, iprodone or vinclozolin;

benzanilide-based compounds such as flutolanil, mepronil, zoxamid or tiadinil;

anilide-based compounds such as carboxin, oxycarboxin, thifluzamide, penthiopyrad, boscalid, fluopicolide, fluopyram or bixafen;

piperazine-based compounds such as triforine;

pyridine-based compounds such as pyrifenox;

carbinol-based compounds such as fenarimol or flutriafol;

piperidine-based compounds such as fenpropidine;

morpholine-based compounds such as fenpropimorph or tridemorph;

organic tin-based compounds such as fentin hydroxide or fentin acetate;

urea-based compounds such as pencycuron;

cinnamic acid-based compounds such as dimethomorph, flumorph or flumetover;

phenylcarbamate-based compounds such as diethofencarb;

cyanopyrrole-based compounds such as fenpiclonil;

strobilurin-based compounds such as kresoxim-methyl, metominofen, metominostrobin, trifloxystrobin, picoxystrobin, oryzastrobin, dimoxystrobin, pyraclostrobin or fluoxastrobin;

oxazolidinone-based compounds such as famoxadone;

thiazole carboxamide-based compounds such as ethaboxam;

silyl amide-based compounds such as silthiopham;

amino acid amide carbamate-based compounds such as benthiavalicarb-isopropyl;

imidazolidine-based compounds such as fenamidone;

hydroxyanilide-based compounds such as fenhexamid;

benzenesulfonamide-based compounds such as flusulfamide;

oxime ether-based compounds such as cyflufenamid;

phenoxyamide-based compounds such as fenoxanil; and antibiotics such as validamycin, kasugamycin or polyoxins;

In addition, examples of other compounds include tolyfluanid, isoprothiolane, pyroquilon, diclomezine, quinoxyfen, spiroxamine, chloropicrin, dazomet, metam-sodium, nicobifen, metrafenone, UBF-307, diclocymet, proquinazid, amisulbrom, pyribencarb, mandipropamid, 5-chlor-7-(4-methyl-piperidin-1-yl)-6-(2,4,6-trifluor-phenyl)-[1,2,4]triazolo[1,5-a]pyrimidin, OK-5203 and the like.

Examples of active ingredient compounds of insecticides, miticides, nematocides or soil pest control agents (generic name, including those for which application is currently pending) include:

organic phosphate ester-based compounds such as profenofos, dichlorvos, fenamiphos, fenitrothion, EPN, diazinon, chlorpyrifos-methyl, acephate, prothiofos, fosthiazate, phosphocarb, cadusafos, dislufoton, chlorpyrifos, demeton-S-methyl, dimethoate, methamidophos, isoxathion, isofenphos, ethion, etrimfos, quinalphos, dimethylvinphos, sulprofos, thiometon, vamidothion, pyraclofos, pyridaphenthion, pirimiphos-methyl, propaphos, phosalone, formothion, malathion, tetraclovinphos, chlorfenvinphos, cyanophos, trichlorfon, methidathion, phenthoate, ESP, azinphos-methyl, fenthion, heptenophos, methoxychlor, paration, monocrotophos, imicyafos, parathion-methyl, terbufos, phospamidon, phosmet or phorate;

carbamate-based compounds such as carbaryl, propoxur, aldicarb, carbofuran, thiodicarb, methomyl, oxamyl, ethiofencarb, pirimicarb, fenobucarb, carbosulfan, benfuracarb, bendiocarb, furathiocarb, isoprocarb, metolcarb, xylylcarb, XMC or fenothiocarb;

nereistoxin derivatives such as cartap, thiocyclam, bensultap or thiosultap-sodium;

organic chlorine-based compounds such as dicofol, tetradifon, endosulufan, dienochloror dieldrin;

organic metal-based compounds such as fenbutatin oxide or cyhexatin;

pyrethroid-based compounds fenvalerate, permethrin, cypermethrin, deltamethrin, cyhalothrin, tefluthrin, ethofenprox, cyfluthrin, fenpropathrin, bifenthrin, flucythrinate, fluvalinate, cycloprothrin, lambda-cyhalothrin, pyrethrins, esfenvalerate, tetramethrin, resmethrin, protrifenbute, zetacypelinethrin, acrinathrin, alpha-cypermethrin, allethrin, gamma-cyhalothrin, theta-cypermethrin, tau-fluvalinate, tralomethrin, profluthrin, beta-cypermethrin, beta-cyfluthrin, metofluthrin or phenothrin;

benzoylurea-based compounds such as diflubenzuron, chlorfluazuron, teflubenzuron, flufenoxuron, lufenuron, novaluron, triflumuron, hexaflumuron, noviflumuron, bistrifluoron or fluazuron;

juvenile hormone-like compounds such as methoprene, pyriproxyfen, fenoxycarb or diofenolan;

pyridazinone-based compounds such as pyridaben;

pyrazole-based compounds such as fenpyroximate, fipronil, tebufenpyrad, ethiprole, tolfenpyrad, acetoprole, pyrafluprole or pyriprole;

neonicotinoids such as imidacloprid, nitenpyram, acetamiprid, thiacloprid, clothianidin, dinotefuran or nithiazine; and, hydrazine-based compounds such as tebufenozide, methoxyfenozide, chromafenozide or halofenozide.

Examples of other compounds include flonicamid, buprofezin, hexythiazox, amitraz, chlordimeform, silafluofen, triazamate, pymetrozine, pyrimidifen, chlorfenapyr, indoxacarb, acequinocyl, etoxazole, cyromazine, 1,3-dichloropropene, diafenthiuron, benclothiaz, flufenerim, pyridalyl, spirodiclofen, bifenazate, spiromesifen, spirotetramat, propargite, clofentezine, fluacrypyrim, metaflumizone, flubendiamide, cyflumetofen, chlorantraniliprole, cyenopyrafen, pyrifluquinazon, fenazaquin, amidoflumet, chlorobenzoate, sulfluramid, hydramethylnon, metaldehyde and ryanodine.

Moreover, additional examples of compounds include crystal protein toxins produced by *Bacillus thuringienses aizawai, Bacillus thuringienses kurstaki, Bacillus thuringienses israelensis, Bacillus thuringienses japonensis, Bacillus thuringienses tenebrionis* or *Bacillus thuringienses*; microbial agricultural chemicals such as insect pathogen viral agents, insect pathogen fungal agents or nematode pathogen fungal agents; antibiotics or semi-synthetic antibiotics such as avermectin, emamectin-benzoate, milbemectin, spinosad, ivermectin or lepimectin;

naturally-occurring substances such as azadirachtin or rotenone;

cooperative agents such as piperonyl butoxide; and repellents such as deet.

(3) Plant Disease Control Agent

The plant disease control agent of the present invention contains at least one of tetrazoyloxime derivatives and at least one of the said other fungicidal active ingredients for agricultural and horticultural use. By using the above two components together, a pronounced plant disease control effect (synergetic effect), which is unpredictable from the effect that is obtained by using the components alone, can be obtained.

In the plant disease control agent of the present invention, the composition ratio between tetrazoyloxime derivatives and the said other fungicidal active ingredient for agricultural and horticultural use is not particularly limited. Although the synergetic effect can be obtained just by using the tetrazoyloxime derivatives together with the said other fungicidal active ingredients for agricultural and horticultural use, the composition ratio between tetrazoyloxime derivatives and the said other fungicidal active ingredients for agricultural and horticultural use is normally 1:10,000,000 to 10,000,000:1, preferably 1:1,000,000 to 1,000,000:1, more preferably 1:100,000 to 100,000:1, particularly preferably 1:10,000 to 10,000:1.

Examples of the method for producing the plant disease control agent of the present invention include (a) a method for producing the plant disease control agent by mixing a preparation containing tetrazoyloxime derivatives and a preparation containing the fungicidal active ingredients for agricultural and horticultural use at a predetermined ratio; (b) a method for producing the plant disease control agent by mixing tetrazoyloxime derivatives and the fungicidal active ingredients for agricultural and horticultural use at a predetermined ratio; (c) a method for producing a plant disease control agent by diluting a predetermined amount of a preparation containing tetrazoyloxime derivatives and a preparation containing the fungicidal active ingredients for agricultural and horticultural use to obtain a water-diluted solution of the plant disease control agent; or the like.

The preparation containing tetrazoyloxime derivatives used in the methods (a) and (c), the preparation containing the said other fungicidal active ingredients for agricultural and horticultural use, and the plant disease control agent obtained by the methods (a) and (b) may be used by a faun able to be adopted by ordinary agricultural chemicals, namely a wettable powder, granules, powder, emulsion, aqueous solution, suspension or flowable agent may be adopted.

Examples of additives and carriers fora the agricultural chemical preparation used for the purpose of solid formulations include vegetable powders such as soybean powder or wheat powder, mineral fine powders such as diatomaceous earth, apatite, gypsum, talc, bentonite, pyrophyllite or clay, and organic and inorganic compounds such as sodium benzoate, urea or sodium sulfate.

In the case of using for the purpose of liquid formulations, oil fraction such as kerosene, xylene, and solvent naphtha; cyclohexane; cyclohexanone; dimethylformamide; dimethylsulfoxide; alcohol; acetone; trichloroethylene; methyl isobutyl ketone; mineral oil; vegetable oil and water; for example; can be used as solvents.

Moreover, a surfactant can be added to these preparations as necessary to obtain a uniform and stable form.

There are no particular limitations on surfactants to be used, and examples include nonionic surfactants such as polyoxyethylene-alkyl phenyl ethers, polyoxyethylene-alkyl ethers, polyoxyethylene-higher fatty acid esters, polyoxyethylene-sorbitan higher fatty acid esters or polyoxyethylene-tristyryl phenyl ether, and sulfuric acid ester salts of polyoxyethylene-alkyl phenyl ethers, alkyl naphthalene sulfonates, polycarboxylates, lignin sulfonates, formaldehyde condensates of alkyl naphthalene sulfonates and isobutylene-maleic anhydrate copolymers.

The concentration of the active ingredient in the plant disease control agent of the present invention (total amount of the tetrazoyloxime derivatives and the said other active ingredients for agricultural and horticultural use) is not particularly limited and can be varied to various concentrations according to the above-described fowl of the preparation and according to need. For example, in the wettable powder, the concentration of the active ingredient is normally 5 to 90% by weight, preferably 10 to 85% by weight; in the emulsion, the concentration of the active ingredient is normally 3 to 70% by weight, preferably 5 to 60% by weight; in the granules, the concentration of the active ingredient is normally 0.01 to 50% by weight, preferably 0.05 to 40% by weight.

The wettable powder, emulsion and flowable agent obtained in this manner may be used in such a manner that the wettable powder, emulsion and flowable agent are diluted with water to a predetermined concentration and the resulting suspension or emulsion is sprayed on soil or mixed with soil before or after germination of weeds. The granules or powder may be directly sprayed on soil or mixed with soil before or after generation of weeds. For example, for applying the plant disease control agent of the present invention, the appropriate amount of the active ingredient is more than 0.1 g per hectare.

In the plant disease control agent of the present invention, an additive agent such as rape oil, soybean oil, sunflower seed oil, castor oil, pine oil, cotton seed oil or derivatives thereof; or oil concentrates thereof may be added.

The plant disease control agent of the present invention may be used by mixing with well-known insecticides, miticides, herbicides, plant growth regulators, fertilizers or the like to decrease the amount used, thereby allowing labor-saving.

EXAMPLES

The following provides a more detailed explanation of the present invention through examples thereof. However, the present invention is not limited to the following examples.

Examples 1 to 29

(1) Agrichemical Component I

As for the agrichemical component I, a suspension agent (SC agent) containing the compound represented by the formula (1) was prepared by the following steps. As for the compound represented by the formula (1), the compound described in Table 3 (compound number (3)-(8)) of International Publication No. WO 03/016303 was used.

| | |
|---|---|
| Compound represented by the formula (1) | 10 parts |
| Polyoxyethylene aryl phenyl ether ether | 2 parts |
| Dialkyl sulfosuccinate sodium salt | 0.5 parts |
| Glycerin | 5 parts |
| Xanthane gum | 0.3 parts |
| Water | 82.2 parts |

These components were mixed and wet-milled until the grain size is reduced to 3 μm or less, thereby obtaining an SC agent containing 10% of active ingredient.

(2) Agrichemical Component II

As for the agrichemical component II, a preparation containing the following components (A) to (O) as the said other fungicidal active ingredient for agricultural and horticultural use was used.

(A) NISSO ALTETTE WP (Active ingredient: fosetyl, amount of active ingredient: 80%, manufactured by Nippon Soda Co., Ltd.)

(B) Doitsu Bordeaux-A (Active ingredient: basic copper chloride, amount of active ingredient: 50% by copper amount, manufactured by HOKKO CHEMICAL INDUSTRY CO., LTD.)

(C) FOLPET simple emulsion [prepared using the commercially available FOLPET (Standard product of FOLPET, manufactured by Wako Pure Chemical Industries, Ltd.)]

(D) NISSO PREVICUR-N LIQUID FORMULATION (Active ingredient: propamocarb hydrochloride, amount of active ingredient: 64%, manufactured by Nippon Soda Co., Ltd.)

(E) Takeda Daconil 1000 (Active ingredient: TPN (chlorothalonil), amount of active ingredient: 40%, manufactured by Sumika-Takeda company)
(F) Diman-Dithane WP (Main component: manzeb, amount of active ingredient: 75%, manufactured by Dow Chemical Japan Ltd.)
(G) Carzate WP (active ingredient: cymoxanil, amount of active ingredient: 50%, manufactured by Du pont kabushiki kaisha)
(H) Bellkute WP (Active ingredient: iminoctadine albesilate, amount of active ingredient: 40%, manufactured by Nippon Soda Co., Ltd.)
(I) Rahman flowable (Active ingredient: cyazofamid, amount of active ingredient: 9.4%, manufacture by ISHIHARA SANGYO KAISHA LTD.)
(J) Subdue Maxx solution (Active ingredient: metalaxyl M, amount of active ingredient: 22.0%, manufactured by Syngenta Japan K.K.)
(K) Savior Flowable 20 (Active ingredient: fludioxonil, amount of active ingredient: 20%, manufacture by Syngenta Japan K.K.)
(L) Silvacur flowable (Active ingredient: tebuconazole, amount of active ingredient: 40%, manufactured by Bayer Holding Ltd.)
(M) JOAO EC (Active ingredient: prothioconazole, amount of active ingredient: 25%, manufactured by Syngenta Japan K.K.)
(N) Actara Water Soluble Granule (Active ingredient: thiamethoxam, amount of active ingredient: 10%, manufactured by Syngenta Japan K.K.)
(O) Amistar-20 FL (Active ingredient: azoxystrobin, amount of active ingredient: 20%, manufactured by Syngenta Japan K.K.)

(3) Preparation of Plant Disease Control Agent

Plant disease control agents of Examples 1 to 13 were prepared by tank-mixing the agrichemical component I and the agrichemical component II in the ratios shown in Table 1 to Table 2.

Furthermore, agrichemical solutions of Examples 14 to 29 were prepared by dissolving the agrichemical component I and the agrichemical component II in sterilized water to adjust the ratio between the agrichemical component I and the agrichemical component II to the ratios shown in Tables 3 to Table 5.

Comparative Examples 1 to 45

Plant disease control agents of the comparative examples were prepared by using the agrichemical component I alone or when using the agrichemical component II alone to adjust the concentrations of the agrichemical component I and the agrichemical component II to the concentrations shown in Tables 1 to 5. In addition, in Comparative Examples 8, 19, 29, 35 and 45, plant disease control agent including the agrichemical component I or the agrichemical component II was not used.

In addition, the concentrations in Tables 1 to 5 show concentrations of the active ingredients of the agrichemical component I and the agrichemical, component II.

The following tests were carried out using the plant disease control agents prepared as described above.

Test Example 1

Tomato Late Blight Prevention Test

Tomato seedlings (variety: Regina, 4th to 5th leaf term) cultivated in terracotta pots were sprayed with the plant disease control agent obtained in the Examples shown in Table 1 at an active ingredient concentration of 50 ppm. After spraying, the plants were allowed to air dry at room temperature, and the test plants were inoculated by spraying with a suspension of zoosporangia of tomato late blight pathogen (*Phytophthora infestans*) and holding for 4 days in a high-humidity, constant temperature chamber (20° C.) at a light/dark cycle of 12 hours. The appearance of lesion on the leaves was compared with untreated plants to determine the prevent value. The results are shown in Table 1 as well as the expected value calculated as follows.

The expected value was calculated using Colby's equation: $E=M+N-MN/100$.

In the equation, E represents expected value of prevent value (%), M represents prevent value obtained when using the agrichemical component I alone (%), N represents prevent value obtained when using the agrichemical component II alone (%).

In addition, comparative examples, in which the agrichemical component I was used alone (Comparative Examples 1 to 2) or the agrichemical component II was used alone (Comparative Examples 3 to 7) instead of the plant disease control agent, were carried out in the same manner as in the above-described example, and also comparative example without treatment (Comparative Example 8) was carried out in the same manner as in the above-described example. The results are shown in Table 1.

TABLE 1

| No. | Agrichemical component I Concentration (ppm) | Agrichemical component II Type | Agrichemical component II Concentration (ppm) | Prevent value | Expected value |
|---|---|---|---|---|---|
| Example 1 | 0.1 | A | 100 | 69 | 34 |
| Example 2 | | B | 25 | 69 | 44 |
| Example 3 | | C | 1.6 | 50 | 25 |
| Example 4 | | D | 100 | 56 | 25 |
| Example 5 | | E | 0.4 | 38 | 25 |
| Comparative Example 1 | 0.4 | — | | 75 | — |
| Comparative Example 2 | 0.1 | — | | 25 | — |
| Comparative Example 3 | — | A | 100 | 13 | — |
| Comparative Example 4 | — | B | 25 | 25 | — |
| Comparative Example 5 | — | C | 1.6 | 0 | — |
| Comparative Example 6 | — | D | 100 | 0 | — |
| Comparative Example 7 | — | E | 0.4 | 0 | — |
| Comparative Example 8 | Without treatment | | | 0 | — |

As shown in Table 1, the prevent value observed in Examples 1 to 5 in which the plant disease control agent was used were larger than the expected value calculated using Colby's equation, and a synergetic effect was demonstrated.

Test Example 2

Cucumber Downy mildew Prevention Test

Cucumber seedlings (variety: Sagami-Hanjiro) cultivated in terracotta pots were sprayed with the plant disease control agent obtained in the examples shown in Table 2 at the active ingredient concentrations shown in the table. After spraying, the plants were allowed to air dry at room temperature, and the test plants were inoculated by spraying with a suspension of spore of cucumber Downy mildew (*Pseudoperonospora cubensis*) and holding for 4 days in a constant temperature chamber (25° C.) at a light/dark and wet/dry cycle of 12 hours. The appearance of lesion on the leaves was compared with untreated plants to determine the prevent value. The results are shown in Table 2 as well as the expected value calculated using the above-described Colby's equation.

In addition, comparative examples, in which the agrichemical component I was used alone (Comparative Examples 9 to 10) and the agrichemical component II was used alone (Comparative Examples 11 to 18) instead of the plant disease control agent, were carried out in the same manner as in the above-described example, and also comparative example without treatment (Comparative Example 19) was carried out in the same manner as in the above-described example. The results are shown in Table 2.

TABLE 2

| No. | Agrichemical component I Concentration (ppm) | Agrichemical component II Type | Agrichemical component II (ppm) | Prevent value | Expected value |
|---|---|---|---|---|---|
| Example 6 | 0.1 | A | 400 | 81 | 44 |
| Example 7 | | B | 25 | 75 | 25 |
| Example 8 | | C | 6.3 | 100 | 72 |
| Example 9 | | D | 400 | 88 | 44 |
| Example 10 | | E | 1.6 | 94 | 63 |
| Example 11 | | F | 6.3 | 99 | 86 |
| Example 12 | | G | 6.3 | 99 | 34 |
| Example 13 | | H | 100 | 94 | 53 |
| Comparative Example 9 | 0.4 | — | | 50 | — |
| Comparative Example 10 | 0.1 | — | | 25 | — |
| Comparative Example 11 | — | A | 400 | 25 | — |
| Comparative Example 12 | — | B | 25 | 0 | — |
| Comparative Example 13 | — | C | 6.3 | 63 | — |
| Comparative Example 14 | — | D | 400 | 25 | — |
| Comparative Example 15 | — | E | 1.6 | 50 | — |
| Comparative Example 16 | — | F | 6.3 | 81 | — |
| Comparative Example 17 | — | G | 6.3 | 13 | — |
| Comparative Example 18 | — | H | 100 | 38 | — |
| Comparative Example 19 | Without treatment | | | 0 | — |

As shown in Table 2, the prevent values observed from the plant disease control agents of Examples 6 to 13 were larger than the expected values calculated using the above-described Colby's equation and a synergetic effect was demonstrated.

Test Example 3

*Pythium aphanidernatum* or *pythium ultimum* Prevention Test

The agrichemical solution obtained in the examples shown in Tables 3 to 5 were added to a PDA culture media to adjust the concentrations of the agrichemical solutions to the concentrations shown in Tables 3 to 5, and agar plates were prepared by adding 1% of the resulting culture media. Than the mycelium disk of *Pythium aphanidermatum* or *Pythium ultimum* was sown in the agar plates. After statically placing the agar plates for 3 to 4 days at 20° C., the colony diameters were measured, and the hyphal elongation inhibition rates of the control group (comparative example without treatment) was calculated as prevent values. The results are shown in Tables 3 to 5 as well as the expected values calculated using the above-described Colby's equation.

The hyphal elongation inhibition rate (%) was calculated using the following equation.

Hyphal elongation inhibition rate (%) (prevent value)
=(1−(colony diameter in the treatment group)/
(colony diameter in the control group))×100%

In addition, Tables 3 and 4 show the results of the comparative examples in which *Pythium* aphanidermatum mycelium disk was used, and Table 5 shows the result of the comparative example in which a *Phythium ultimum* mycelium disk was used.

Furthermore, comparative examples, in which the agrichemical component I was used alone (Comparative Examples 20 to 21, Comparative Examples 30 to 31, Comparative Examples 36 to 37) and the agrichemical component II was used alone (Comparative Examples 22 to 28, Comparative Examples 32 to 34, Comparative Examples 38 to 44) instead of the plant disease control agent, were carried out in the same manner as in the above-described example, and also comparative examples without treatment (Comparative Examples 29, 35, 45) were carried out in the same manner as in the above-described example. The results are shown in Tables 3 to 5.

TABLE 3

| No. | Agrichemical component I Concentration (ppm) | Agrichemical component II Type | Agrichemical component II Concentration (ppm) | Prevent value | Expected value |
|---|---|---|---|---|---|
| Example 14 | 0.0001 | I | 0.01 | 100 | 69 |
| Example 15 | | J | 0.01 | 100 | 83 |
| Example 16 | | E | 0.1 | 100 | 50 |
| Example 17 | | D | 1 | 91 | 46 |
| Example 18 | | K | 100 | 99 | 62 |
| Example 19 | | L | 10 | 95 | 66 |
| Example 20 | | M | 10 | 93 | 61 |
| Comparative Example 20 | 0.01 | — | | 80 | — |
| Comparative Example 21 | 0.0001 | — | | 37 | — |
| Comparative Example 22 | — | I | 0.01 | 51 | — |
| Comparative Example 23 | — | J | 0.01 | 74 | — |
| Comparative Example 24 | — | E | 0.1 | 21 | — |
| Comparative Example 25 | — | D | 1 | 14 | — |
| Comparative Example 26 | — | K | 100 | 40 | — |
| Comparative Example 27 | — | L | 10 | 46 | — |
| Comparative Example 28 | — | M | 10 | 39 | — |
| Comparative Example 29 | Without treatment | | | 0 | — |

TABLE 4

| No. | Agrichemical component I Concentration (ppm) | Agrichemical component II Type | Agrichemical component II Concentration (ppm) | Prevent value | Expected value |
|---|---|---|---|---|---|
| Example 21 | 0.0001 | N | 10 | 57 | 1 |
| Example 22 | 0.0001 | O | 10 | 81 | 35 |
| Example 23 | 0.0001 | L | 1 | 32 | 4 |
| Comparative example 30 | 0.01 | — | — | 56 | — |
| Comparative example 31 | 0.0001 | — | — | 1 | — |
| Comparative example 32 | — | N | 10 | 0 | — |
| Comparative example 33 | — | O | 10 | 34 | — |
| Comparative example 34 | — | L | 1 | 2 | — |
| Comparative example 35 | Without treatment | | | 0 | — |

TABLE 5

| No. | Agrichemical component I Concentration (ppm) | Agrichemical component II Type | Agrichemical component II Concentration (ppm) | Prevent value | Expected value |
|---|---|---|---|---|---|
| Example 24 | 0.0001 | I | 0.01 | 87 | 6 |
| Example 25 | 0.0001 | J | 0.01 | 91 | 71 |
| Example 26 | 0.0001 | E | 0.1 | 74 | 0 |
| Example 27 | 0.0001 | D | 1 | 68 | 0 |
| Example 28 | 0.0001 | K | 100 | 77 | 0 |
| Example 29 | 0.0001 | L | 10 | 73 | 0 |
| Comparative example 36 | 0.01 | — | — | 51 | — |
| Comparative example 37 | 0.0001 | — | — | 0 | — |
| Comparative example 38 | — | I | 0.01 | 6 | — |
| Comparative example 39 | — | J | 0.01 | 71 | — |
| Comparative example 40 | — | E | 0.1 | 0 | — |
| Comparative example 41 | — | D | 1 | 0 | — |
| Comparative example 42 | — | K | 100 | 0 | — |
| Comparative example 43 | — | L | 10 | 0 | — |
| Comparative example 44 | — | M | 10 | 28 | — |
| Comparative example 45 | Without treatment | | | 0 | — |

As shown in Tables 3 to 5, the prevent values obtained when using the agrichemical solutions containing the agrichemical component I and the agrichemical component II were larger than the expected values calculated by substituting the prevent values obtained when using the agrichemical component I alone or when using the agrichemical component II alone into the above describe Colby's equation. In addition, the prevent value obtained when using the plant disease control agent containing the agrichemical component I and agrichemical component II was larger than the prevent value of the comparative examples without treatment. Therefore, a synergetic effect by using the agrichemical component I together with the agrichemical component II was demonstrated.

Industrial Applicability

The plant disease control agent of the present invention demonstrates excellent control effects against plant disease at low doses, and eliminates concern over chemical damage to useful plants, thereby making it industrially useful.

The invention claimed is:
1. A plant disease control agent comprising at least one of tetrazoyloxime derivatives represented by a formula (1) and salts thereof,

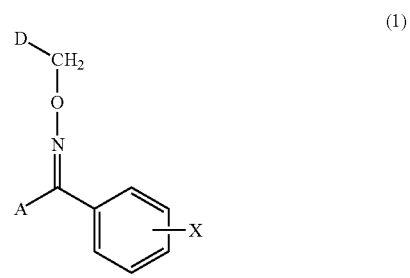

(1)

wherein, X represents hydrogen atom, a C1 to C6 alkyl group, a C1 to C6 alkoxy group, halogen atom, nitro group, cyano group, a C6 to C10 aryl group or a C1 to C6 alkyl sulfonyl group,
A represents a tetrazoyl group represented by a formula (2) or (3)

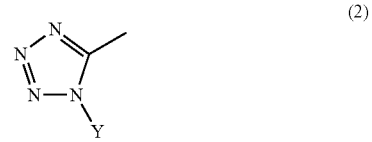

(2)

(3)

wherein, Y represents a C1 to C6 alkyl group,
D represents a group represented by a formula (4) or (5)

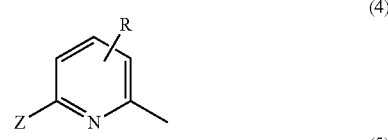

(4)

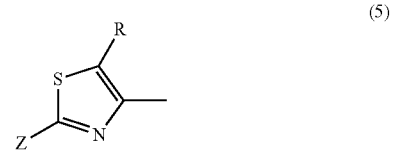

(5)

wherein, Z represents hydrogen atom, an amino group or a group represented by a formula —NHC(=O)—Q,
wherein, Q represents hydrogen atom, a C1 to C8 alkyl group, a C1 to C6 haloalkyl group, a C3 to C6 cycloalkyl group, a C1 to C8 alkoxy group, a C3 to C6 cycloalkyloxy group, a C7 to C20 aralkyloxy group, a C1 to C4 alkyl thio C1 to C8 alkyl group, a C1 to C4 alkoxy C1 to C2 alkyl group, a C1 to C4 acyl amino C1 to C6 alkyl group, a C1 to C4 acyl amino C1 to C6 alkoxy group, a C1 to C8 alkyl amino group, a C2 to C6 alkenyl group, an aralkyl group or phenyl group, R represents hydrogen atom or a halogen atom, and at least one agent selected from the group consisting of fosetyl, basic copper chloride, chlorothalonil, manzeb, cymoxanil, folpet, cyazofamid, metalaxyl, fludioxonil, tebuconazole, azoxystrobin, propamocarb hydrochloride, iminoctadine triacetate and iminoctadine trialbesilate.

* * * * *